United States Patent [19]

Armstrong et al.

[11] Patent Number: 4,660,423
[45] Date of Patent: Apr. 28, 1987

[54] WATER SAMPLING APPARATUS

[76] Inventors: John M. Armstrong, 2480 Gale Rd.; Michael E. Ettenhofer, 3737 Northfield Church Rd., both of Ann Arbor, Mich.

[21] Appl. No.: 853,582

[22] Filed: Apr. 18, 1986

[51] Int. Cl.[4] .............................................. G01N 1/14
[52] U.S. Cl. .................. 73/864.52; 73/864.91
[58] Field of Search ........... 73/864.52, 864.51, 864.63, 73/864.64, 864.65, 864.66, 864.67, 864.91, 863.81

[56] References Cited

U.S. PATENT DOCUMENTS

| 3,026,730 | 3/1962 | Howarth et al. | 73/864.66 |
| 3,886,800 | 6/1975 | Boehringer | 73/864.63 |
| 4,300,404 | 11/1981 | Mehl et al. | 73/864.91 |
| 4,438,634 | 3/1984 | Torstensson | 166/264 |

*Primary Examiner*—Michael J. Tokar
*Assistant Examiner*—Robert R. Raevis

[57] ABSTRACT

Apparatus for taking water samples from wells, streams, lakes, or the like wherein the water sample is to be duplicative of the water that is being tested. The apparatus consists of a carrier adapted to be lowered on a line to any depth into the water body to be sampled. The carrier is hollow and has an internal load carrying cavity in which a unit consisting of an isolation vial filled with distilled water and a sample collection vial which is evacuated and positioned within the isolation vial are loaded. Both vials are equipped with closing plugs therein which contain septums and a hollow needle structure is provided which pierces the isolation vial septum and extends into but does not pierce the sample collecting septum. In response to a jerk on the line, the carrier exerts a force on the needle unit which causes it to pierce the spectum in the sample vial thereby communicating the interior of the sample vial with the water to be sampled, with the result that a sample of the water to be tested rushes into the sample vial. The lowing line can then be raised so as to raise the carrier with the desired water sample therein for subsequent testing purposes.

4 Claims, 5 Drawing Figures

WATER SAMPLING APPARATUS

BACKGROUND OF THE INVENTION

There are many instances in which samples of water from wells, lakes, streams, etc. or other water volumes deep below the earth's surface are desired for test purposes. In such cases, it is essential that the sample be dupicative of the deep water that is to be tested because in many cases the tests on the sample are for the purpose of detecting minute quantities of certain substances in the sample. The principal object of this invention, therefore, is to provide versatile apparatus that is capable of obtaining such samples.

SUMMARY OF THE INVENTION

The apparatus of this invention utilizes sample units which are prepared and stored for quick use when samples of well water or the like are desired. These sample units consist of a pair of test tube shape vials positioned one within the other. The outer vial hereinafter referred to as the "isolation vial" is filled with distilled water and plugged at its open end so that it will not leak, the plug containing a thin wall section hereinafter referred to as the "septum". The inner vial, hereinafter referred to as the "sample vial", is evacuated so that it contains a vacuum and is plugged at its open end so as to maintain the vacuum within the vial. The plug in the sample vial also contains a septum that is aligned in a direction axially of the vial with the septum in the isolation vial.

A needle unit consisting of a head member and a hollow needle member mounted at one end on and extending through the head member and having a point at the opposite end is assembled with the vials by extending the needle through the isolation vial septum and either into or close to the sample vial septum without piercing the sample vial septum. The head of the needle unit is maintained in a spaced relation with the isolation vial plug by a spacer removably positioned therebetween so as to positively preclude piercing of the sample vial septum until the spacer is removed.

The apparatus also includes a carrier member for lowering the sample unit into the water to be sampled. The carrier is of somewhat bullet shape having a generally flat lower end and a pointed upper end so that it can be withdrawn from a lowered positioned past obstructions in a narrow passageway. It can be lowered into any body of water such as a well without any modification to the well, as required in the structure shown in prior art U.S. Pat. No. 4,438,654. The carrier is hollow having a load carrying cavity into which the sample unit is positioned with the head member for the needle unit positioned against a reaction force surface at the lower end of the carrier. The spacer is removed just prior to lowering the carrier into the water.

The carrier is then lowered into the water to be tested which flows into the carrier and into the lower open end of the needle member. A trigger mechanism, or similar device, is operated from above to jerk the lowering line and thereby cause the lower end of the carrier to exert an upwardly directed force on the head member carrying the hollow needle member so as to thrust the sharp end of the needle upwardly through the septum closing the sample vial. The vacuum in the sample vial then causes the water from the surrounding area to flow into the sample vial so as to fill it, following which the carrier is raised and the sample vial is removed for testing to accurately determine the nature of the water body from which the sample was removed.

The advantage of the storage of the evacuated sample vial within the isolation vial is to maintain the integrity of the sample and to assure that the vacuum within the sample vial has been maintained at the time that the sample unit is loaded into the carrier. The result is a sampling apparatus that can be used continuously to accurately sample water sources such as wells, streams, lakes, oceans, and the like.

Further objects, features and advantages of the invention will become apparent from a consideration of the following description and the appended claims when taken in connection with the accompanying drawing in which:

Figure 1:
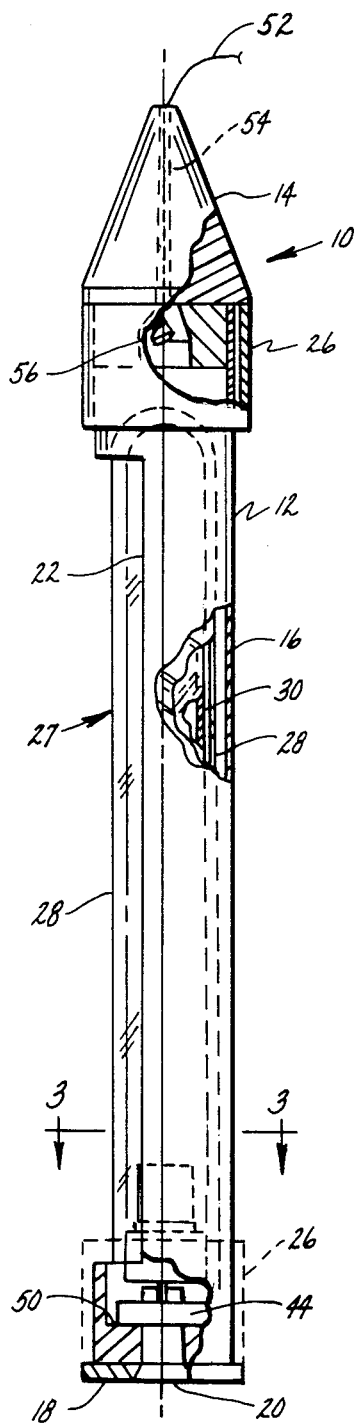
FIG. 1 is a side elevational view of the water sampling apparatus of this invention with some parts broken away and other parts shown in section for the purpose of clarity.
Figure 4:
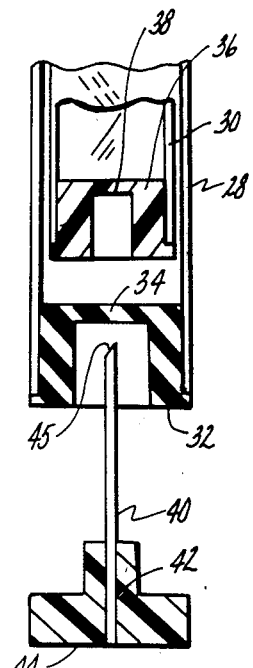
FIG. 4 is a fragmentary sectional view of a portion of the sample unit in the apparatus of this invention.

With reference to the drawing, the water sampling apparatus of this invention, indicated generally at 10, is shown in FIG. 1 as consisting of a carrier 12 of generally bullet shape and formed of metal or other suitable equivalent material. The carrier 12 has a tapered upper end portion 14, a tubular side wall portion 16 and a flat bottom wall portion 18 provided with a water inlet 20. The side wall portion 16 is formed with an elongated opening 22 which communicates with a load carrying cavity 24 formed within the side wall portion 16. A ring shape retainer 26 is movable between the upper position shown in full lines in FIG. 1 in which the loading opening 22 is open for loading purposes and the lower retaining position shown in broken lines in FIG. 1 in which the retainer 26 extends over the lower end of the loading opening 22 so as to retain a sample unit 27 to be hereinafter described within the chamber 24. As shown in FIG. 1, the unit 27 is slightly longer than the slot 22 and when the retainer ring 26 is in its retaining position the effective length of the slot 22 is reduced further so that the unit 27 cannot fall out of cavity 24.

A sample unit 27 consists of a pair of test tube shaped vials 28 and 30 (FIG. 2) formed of glass or a suitable transparent plastic and positioned so that the vial 30 is contained within the vial 28. The vial 28 is filled with distilled water 29 and is hereinafter referred to as the isolation vial. The vial 28 has its lower end closed by a plug 32 so as to retain the distilled water within the vial 28, the plug 32 having a reduced thickness section 34 hereinafter referred to as a "septum".

Figure 2:
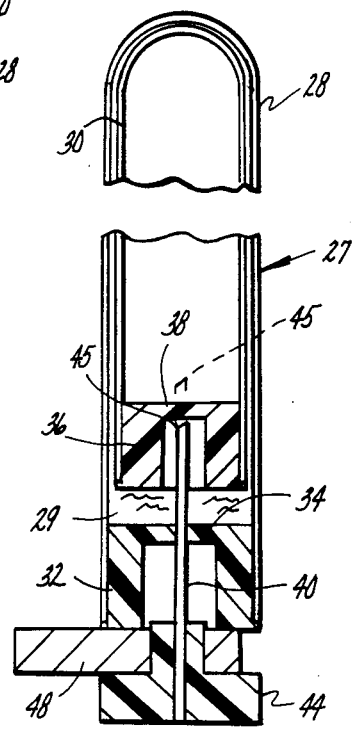
FIG. 2 is a fragmentary perspective view of a portion of the apparatus of this invention.
Figure 5:
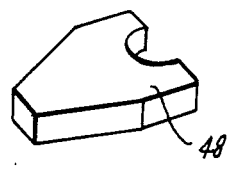
FIG. 5 is a perspective view of a spacer used in the unit shown in FIG. 4.
Figure 3:
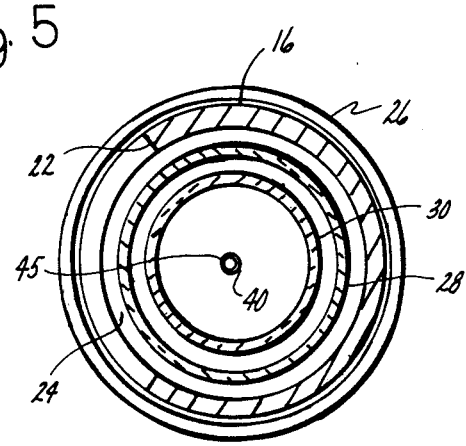
FIG. 3 is an enlarged transverse sectional view of the apparatus of this invention as seen from substantially the lines 3—3 in FIG. 1.

The vial 30 which is contained within the vial 28 and is hereinafter referred to as the sample vial is evacuated so that it contains a vacuum and the vacuum is maintained by a plug 36 in the open end of the vial 30 which likewise has a septum 38 that is aligned, in a direction axially of the vial, with the septum 34. The vial 30 floats in the water 29 in the vial 28 so that the top end of the vial 30 engages the upper end of the vial 28, as shown in FIG. 2. A hollow needle member 40 has one of its ends 42 mounted in and extended through a head member 44 and has its opposite pointed end 45 extended through the septum 34 and into a position only slightly piercing or adjacent the septum 38 so that the needle 40 does not extend beyond the septum 38. The head 44 is maintained in a spaced relation with the plug 32 by positioning a spacer member 48 between the head 44 and the plug 32. The spacer 48 thus prevents piercing of the septum 38.

In the apparatus 10 it is expected that a large number of units 27 will be prepared and placed in storage for use with one or more carriers 12 in water sampling operations. When it is desired to sample a body of water, one of the units 27 is removed from storage and visual examination will show whether or not the vacuum in the sample vial 30 has been maintained during storage. If the sample vial 30 has leaked, it will contain distilled water from the isolation vial 28.

Presuming that the unit 27 that has been selected is suitable, the retainer ring 26 is moved to its upper position so as to fully expose the loading opening 22 and the unit 27 is loaded into the cavity 24 as shown in FIG. 1 so that the needle head 44 is positioned in engagement with an abutment plate 50 at the lower end of the cavity. The retainer ring 26 is then moved to its lower retaining position and a line 52 on which the carrier 12 is supported is manipulated so as to lower the carrier 12 into the body of water to be tested.

As shown in FIG. 1, the line 52 extends downwardly through a passage 54 in the carrier upper end portion 14 and is provided with a crimped retainer 56 at its lower end which prevents the line from being withdrawn through the passage 54. When the carrier 12 has been lowered to a position in which it is in the water to be sampled, a dynamic jerking force is applied to the line 52 so that the carrier 12 will be manipulated so that the plate 50 will exert a large upwardly directed force on the head member 44 driving the needle point 45 through the septum 38 so as to communicate the interior of the sample vial 30 with the water to be tested which enters the carrier cavity 24 through the inlet 20. The vacuum atmosphere within the vial 30 insures flow of water to be tested into the sample vial 30. The plugs 32 and 36 are formed of relatively soft plastic or equivalent material so that they can readily be pierced by the needle 40. After removal of the needle 40 from the plugs, the septums 34 and 38 will tend to re-seal and close the openings formed therein by the needle 40.

The line 52 is then manipulated to raise the apparatus 10, following which the sample unit 27 can be readily removed from the carrier 12 after the retainer ring 26 has been moved to its upper position. The needle is then removed to allow the septum 38 to close, following which the sample vial 30 is stored in the inverted position shown until testing of the vial contents is desired.

From the above description, it is seen that this invention provides apparatus 10 which can be readily used to obtain water samples without introducing contaminants into the water and without first disturbing the body of water that is to be tested so as to insure that a representative sample is obtained.

What is claimed is:

1. Water sampling apparatus comprising a carrier adapted to be lowered into water to be sampled, said carrier being hollow and having an internal load carrying cavity, an isolation vial positioned in said carrier and having a lower end closed by a septum and filled with distilled water, a sample collection vial in said isolation vial having a septum aligned with said septum on said isolation vial, and hollow needle means piercing said septum on said isolation vial and operable to pierce said septum on said sample vial, said needle means being movable in response to a force generated by said carrier to pierce said septum on said sample vial, said needle means communicating said sample vial with said water to be sampled.

2. Apparatus according to claim 1 wherein said carrier includes abutment means at the lower end of said cavity engageable with said needle means to generate said force in response to a dynamic upward movement of said carrier.

3. For use in water sampling apparatus, a test tube shaped isolation vial containing distilled water and having an open end, plug means closing said end and including a septum, an evacuated test tube shaped sample vial enclosed within said isolation vial and having an open end, plug, means closing said end of said sample vial and including a septum substantially aligned with said septum on said isolation vial, a needle unit comprising a head member and a hollow needle member mounted at one end on and extending through said head member and having a pointed opposite end, said needle member extending at its pointed end through said septum on said isolation vial to a position nearly extending through said septum on said sample vial and said head member being positioned in a spaced relation with and adjacent said plug means closing the open end of said isolation vial.

4. Apparatus according to claim 3 further including a spacer member disposed between said head member and said isolation vial maintaining said head member spaced from said isolation vial to preclude movement of said needle point through said septum in said sample vial.

* * * * *